US007914612B2

(12) United States Patent
Rubey et al.

(10) Patent No.: US 7,914,612 B2
(45) Date of Patent: Mar. 29, 2011

(54) COMPLIANT COLUMN SHEATH ASSEMBLY FOR GAS CHROMATOGRAPHY

(75) Inventors: Wayne A. Rubey, Vandalia, OH (US); Richard C. Striebich, Dayton, OH (US); Jesse Contreras, Orem, UT (US)

(73) Assignee: University of Dayton, Dayton, OH (US)

(*) Notice: Subject to any disclaimer, the term of this patent is extended or adjusted under 35 U.S.C. 154(b) by 417 days.

(21) Appl. No.: 11/914,778

(22) PCT Filed: May 19, 2006

(86) PCT No.: PCT/US2006/019523
§ 371 (c)(1),
(2), (4) Date: May 23, 2008

(87) PCT Pub. No.: WO2006/127490
PCT Pub. Date: Nov. 30, 2006

(65) Prior Publication Data
US 2009/0211436 A1   Aug. 27, 2009

Related U.S. Application Data

(60) Provisional application No. 60/683,430, filed on May 20, 2005.

(51) Int. Cl.
*B01D 53/02* (2006.01)
(52) U.S. Cl. ............ 96/101; 73/23.39; 73/23.42; 95/82; 95/87
(58) Field of Classification Search .................. 73/23.35, 73/23.39, 23.42; 95/82, 87; 96/101
See application file for complete search history.

(56) References Cited

U.S. PATENT DOCUMENTS

| 4,805,441 | A | * | 2/1989 | Sides et al. ................... 73/23.25 |
| 4,923,486 | A |   | 5/1990 | Rubey |
| 5,005,399 | A | * | 4/1991 | Holtzclaw et al. ........... 73/23.39 |
| 5,028,243 | A |   | 7/1991 | Rubey |
| 5,114,439 | A |   | 5/1992 | Yost et al. |
| 5,552,042 | A | * | 9/1996 | Le Febre et al. ........... 210/198.2 |
| 5,782,964 | A |   | 7/1998 | Mustacich |
| 5,846,293 | A |   | 12/1998 | Rubey et al. |
| 6,126,728 | A | * | 10/2000 | Walsh et al. .................... 96/101 |
| 6,209,386 | B1 | * | 4/2001 | Mustacich et al. ........... 73/23.39 |

(Continued)

FOREIGN PATENT DOCUMENTS

| EP | 0729028 A1 | 8/1996 |
| GB | 838189 | 7/1958 |

OTHER PUBLICATIONS

Wayne A. Rubey, "An instrument assembly for studying operational behavior of thermal gradient programed gas chromatography", American Institute of Physics, Sep. 1994.

(Continued)

*Primary Examiner* — Michael A Marcheschi
*Assistant Examiner* — Robert A Clemente
(74) *Attorney, Agent, or Firm* — Dinsmore & Shohl LLP

(57) ABSTRACT

A compliant column sheath assembly for use in a gas chromatograph is provided which includes an open tubular column in the form of a helical coil having a coiled length of between about 5 and 15 cm. The sheath assembly further includes an insulating sheath which surrounds the open tubular column and a frame. When incorporated in a gas chromatograph, the compliant column sheath assembly allows samples to be analyzed in about 2 to 10 seconds.

10 Claims, 3 Drawing Sheets

U.S. PATENT DOCUMENTS

| | | | |
|---|---|---|---|
| 6,497,138 | B1 | 12/2002 | Abdel-Rahman et al. |
| 7,067,307 | B2 * | 6/2006 | Hochleitner et al. ...... 435/297.2 |
| 7,291,203 | B2 * | 11/2007 | Crnko et al. ...................... 95/87 |
| 7,524,363 | B2 * | 4/2009 | Bentley et al. .................. 96/101 |

OTHER PUBLICATIONS

Wayne A. Rubey, "Futuristic Health Care and Separation Science", Presentation given at Consiglio Nazionale delle Ricerche in Bari, Italy, pp. 1-11, Oct. 10, 1994.

Wayne A. Rubey, "The Imposition of Time-Programmed 3-and 4-Dimensional Fields Upon Open Tubular Gas Chromatographic Colums", 32nd Annual Rocky Mountain Conference on Analytical Chemistry in Denver, Colorado on Jul. 30, 1990.

Wayne A. Rubey, Theory of Constrained Migration Behavior in Open-Tublar Gas Chromatographic Colums with Various Operational Modes, 23rd International Symposium on Capillary Chromatography, Riva Del Garda, Italy, Jun. 2000.

* cited by examiner

COMPLIANT COLUMN SHEATH ASSEMBLY FOR GAS CHROMATOGRAPHY

CROSS REFERENCE TO RELATED APPLICATIONS

This application claims priority to and is a national application filed under 35 U.S.C. §371 of PCT international application No. PCT/US2006/019523 filed May 19, 2006, which claims priority to U.S. provisional patent application Ser. No. 60/683,430 filed May 20, 2005, both of which are hereby incorporated by reference in their entirety.

The present invention relates to a compliant column sheath assembly for use with a gas chromatograph, and more particularly, to a column sheath assembly which utilizes an open tubular column in the form of a small helical coil to achieve rapid analysis of individual analytes or samples.

Gas chromatography (GC) was introduced in 1951 and is now the most widely used instrumental chemical analysis technique. The use of GC allows various components of a volatile sample to be separated and detected. Typically, a gas chromatograph includes an inlet into which the sample is injected, a carrier gas delivery system using helium, nitrogen, or hydrogen, a column in which the various analytes are separated, an oven for heating the column/sample, and an outlet through which the separated analytes may pass to a detection device such as a hydrogen flame ionization detector or a fast mass spectrometer which allows detection and identification of the analytes. The column of the gas chromatograph is typically formed from fused silica and is in the form of a narrow, elongated tube, referred to as an open tubular column (OTC). Such columns are typically configured in a coil shape as shown in commonly-assigned U.S. Pat. No. 5,846,293.

As is known in the art, gas chromatographs are often heated in a programmed manner which increases the temperature of the entire column at a steady rate in order to improve the speed with which analytes can be eluted from the column. Techniques which utilize heat include isothermal gas chromatography (ITGC), programmed-temperature gas chromatography (PTGC), and thermal gradient programmed gas chromatography (TGPGC). These analyses are currently conducted with analytical turnaround times that range from approximately one minute up to an hour in duration. However, there has been a desire to be able to perform faster analyses of complex samples in order to allow gas chromatography to be used in a wider variety of applications, including in medical applications such as blood or bodily fluid monitoring, drug testing, breath analysis, health monitoring; in environmental applications such as water, soil, and air analysis; in the petrochemical field; in analysis of the food products, and in monitoring emissions of pollutants.

Accordingly, there is still a need in the art for a gas chromatographic apparatus which allows various analytes to be separated and analyzed at a much faster rate than with current methods.

The present invention meets that need by providing a compliant column sheath assembly (CCSA) which may be used in a gas chromatograph. The CCSA utilizes an open tubular column which is tightly wound into a very small helical coil so that the coiled form of the column is only about 10 cm in length. The configuration of the compliant column sheath assembly allows extremely rapid GC analyses (about 2 to 10 seconds) with negligible recycle time (i.e., the cool-down period normally needed between analysis cycles to reduce the temperature of the column from the final temperature of one determination to the initial temperature of the next determination). The CCSA of the present invention may be readily used in various modes of gas chromatography which use a time-programmed thermal field, including isothermal gas chromatography (ITGC), programmed-temperature gas chromatography (PTGC), programmed-flow gas chromatography (PFGC), thermal gradient programmed gas chromatography (TGPGC), and multi-dimensional gas chromatography (MDGC).

According to one aspect of the present invention, a compliant column sheath assembly (CCSA) for use in a gas chromatograph is provided. By "compliant," it is meant that the CCSA is both physically and thermally compliant, i.e., it withstands different gas flow rates (e.g. bidirectional flows; swirling flows) and rapidly changing gas flows without introducing a large pressure drop within the assembly; and the temperature of the OTC can be changed rapidly so as to maintain a negative thermal gradient within the OTC during analysis. For example, the CCSA must be able to transition from temperatures of less than about −60° C. to greater than 300° C. in less than one second.

The compliant column sheath assembly comprises an open tubular column in the form of a helical coil having front and back ends, and a frame. The column, when mounted, has a length of from about 5 to 15 cm in coiled form. By "mounted," it is meant that the column is mounted into the frame of the CCSA. The frame functions to support the open tubular column and maintain the column in its coiled shape. The frame is preferably in the form of a fine wire metal grid.

The open tubular column preferably has an overall length of about 10 cm in its coiled form. Preferably, the open tubular column comprises fused silica tubing.

The compliant column sheath assembly preferably further comprises an insulating sheath. In one embodiment of the invention, the insulating sheath surrounds the open tubular column and frame. In another embodiment, the frame is embedded in the insulating sheath. In yet another embodiment, the frame is positioned inside or outside of the insulating sheath. The insulation sheath is preferably comprised of a material selected from the group consisting of woven, braided, thin films, non-woven polyimide, or fiberglass.

The compliant column sheath assembly preferably further comprises a cylindrical sleeve which fits inside the column.

The CCSA also preferably further includes a heat exchange gas for regulating the heat and cooling of the open tubular column. The heat exchange gas preferably comprises nitrogen or compressed air. The heat exchange gas allows the temperature of the OTC to be controlled so as to provide a negative axial thermal gradient along the length of the column during analysis. By a "negative thermal gradient," we mean that the temperature in the column decreases as the solutes in the sample migrate along the column.

According to another embodiment of the invention, a gas chromatograph is provided which comprises a compliant column sheath assembly including an open tubular column in the form of a helical coil having a length of from about 5 to 15 cm in coiled form; an insulating sheath surrounding the open tubular column, and a frame for supporting the open tubular column and the sheath. The apparatus further includes a sample inlet region at the front end of the column and a sample outlet region at the back end of the column; where the sample travels from the inlet region to the outlet region.

The gas chromatograph preferably further includes a detector for analyzing samples as they exit the gas chromatograph. Samples introduced into the gas chromatograph may be analyzed in about 2 to 10 seconds.

The present invention also provides a method of analyzing a sample in a gas chromatograph incorporating the CCSA of the present invention which comprises admitting a sample into the open tubular column, wherein the open tubular column has been cooled; and rapidly heating the front end of the open tubular column such that a negative temperature gradient is produced along the length of the column. The sample is analyzed in about 2 to 10 seconds.

Accordingly, it is a feature of the present invention to provide a compliant column sheath assembly for use in gas chromatographs which provides rapid analysis of about 2 to 10 seconds per sample. Other features and advantages of the invention will be apparent from the following description.

The use of a compliant column sheath assembly in accordance with the present invention allows rapid gas chromatography analysis, increased analytical throughput, and an improvement in detection sensitivity. We have found that by providing an open tubular column (OTC) in the form of a small, tightly wound helically coil, the OTC, when mounted in a gas chromatograph, may be heated much more rapidly than previous OTCs with unexpectedly high resolution of the resulting analytical peaks. While not being bound to any particular theory, we believe that the high resolution results from providing a time-related thermal field wherein relative solute velocities, i.e., $\Delta v_s/v_s$ for migrating solutes, remain nearly fixed during the large thermal change that occurs in the gas chromatography program. The CCSA allows the thermal field to be optimized so as to improve the resolution per unit time.

The use of a heat exchange gas in the CCSA of the present invention also provides an advantage in that it allows the gas chromatograph apparatus to be simpler in design as the heat exchange gas eliminates the need for a time-programmed oven or other heat source such as an electrical resistance heating element typically used in gas chromatographs.

Figure 1A:
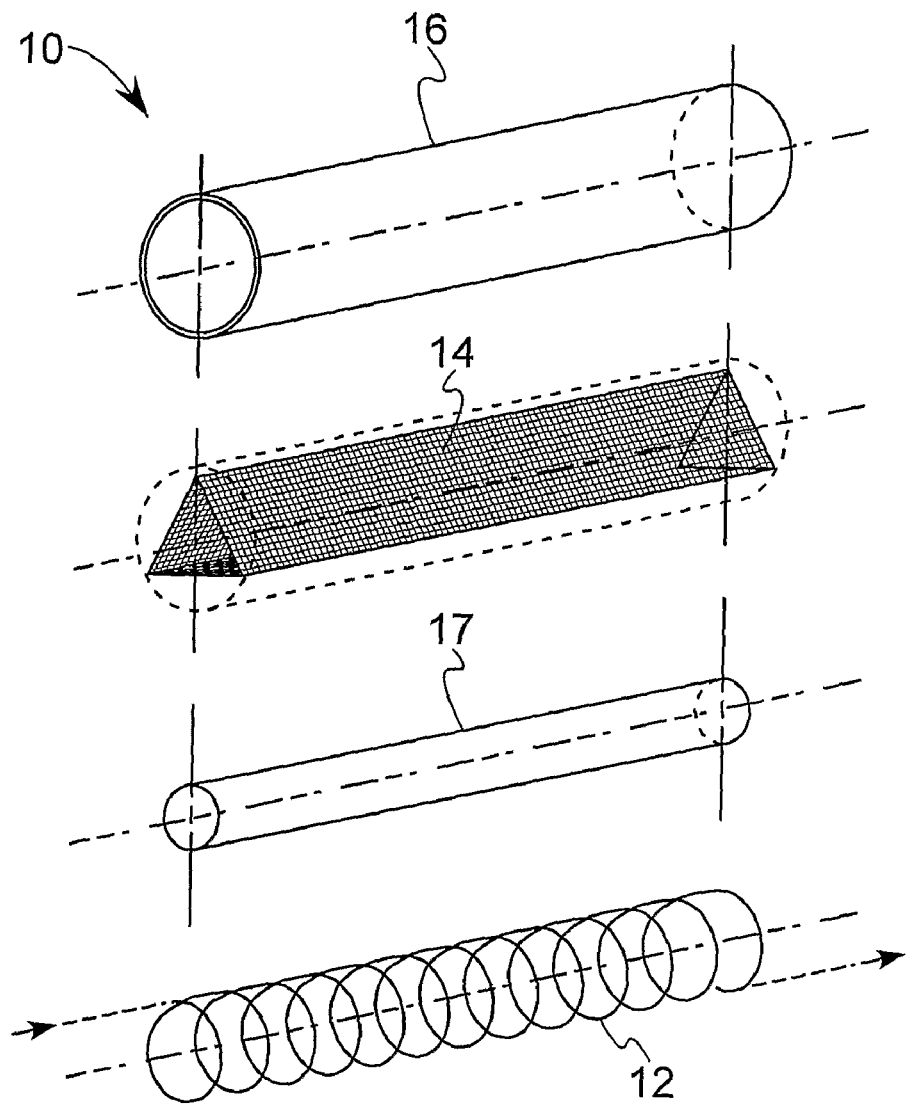
FIG. 1A is a schematic illustration of the individual components of the compliant column sheath assembly of the present invention.
Figure 1B:
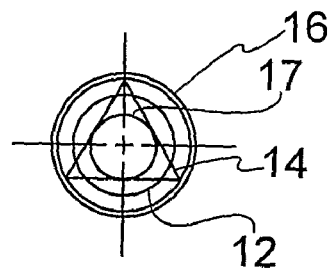
FIG. 1B is an end view of the compliant column sheath assembly.

Referring now to FIG. 1, a compliant column sheath assembly in accordance with the present invention is shown. The CCSA 10 includes an open tubular column 12, a frame 14, and an insulating sheath 16. The CCSA further includes a cylindrical sleeve 17 preferably comprised of polyimide tubing which fits inside the column and functions to contain the column for gas flow. The open tubular column is preferably comprised of fused silica tubing having a polyimide coating on its outer surface. However, it should be appreciated that the column may be comprised of other suitable materials. The polyimide coating functions to protect the fused silica from damage such as cracking, etc. The CCSA preferably comprises a small bore OTC, but columns of other bore widths may also be used. The fused silica tubing preferably has an inner diameter of 0.10 mm and an outer diameter of 170 microns. The inner surface of the fused silica tubing also includes a stationary phase, for example, a polysiloxane film.

The OTC, when provided in straight form, is about 1 to 5 meters in length, and when helically coiled, is about 10 cm in length. This is in direct contrast to previous OTCs which have a gas path of about 30 meters in length. Due to the wound helical coil configuration of the OTC, the CCSA of the present invention has a very low thermal mass, which contributes to the ability of the CCSA to be heated or cooled very rapidly, and thus, resulting in rapid analysis of samples.

The frame 14 is preferably in the form of a fine metal wire grid comprising a metal such as stainless steel, tungsten, or aluminum mesh. However, the frame may comprise any material which is capable of providing the required support for the OTC and the insulation sheath. The fine wire grid functions as a frame, support, or harness around which the fused silica tubing is placed to form a coiled or spiraled configuration which can have various radial and longitudinal patterns. The grid also functions to maintain the small helical coil within its prescribed geometric tolerances, preventing the coil from collapsing. It should be appreciated that the fine-wired frame 14 should preferably have as little contact as possible with the OTC tubing to avoid any localized thermal non-uniformities or heat transfer.

The insulating sheath 16 preferably surrounds the frame and OTC and is preferably in the form of a thin-walled sleeve comprised of woven, braided or non-woven polyimide, fibers, fiberglass or composites containing those materials, or a heat-resistant woven textile such as Zylon®. Any woven, braided, or non-woven insulating materials may be used which provide the required insulating properties. The insulating sheath functions to insulate and centrally position the OTC within the sheath while maintaining radial temperature uniformity. The outer diameter of the sleeved and coiled OTC assembly is about 2.5 cm. While the frame can be positioned inside or outside of the sheath, it is preferably placed inside the sheath.

Figure 2:
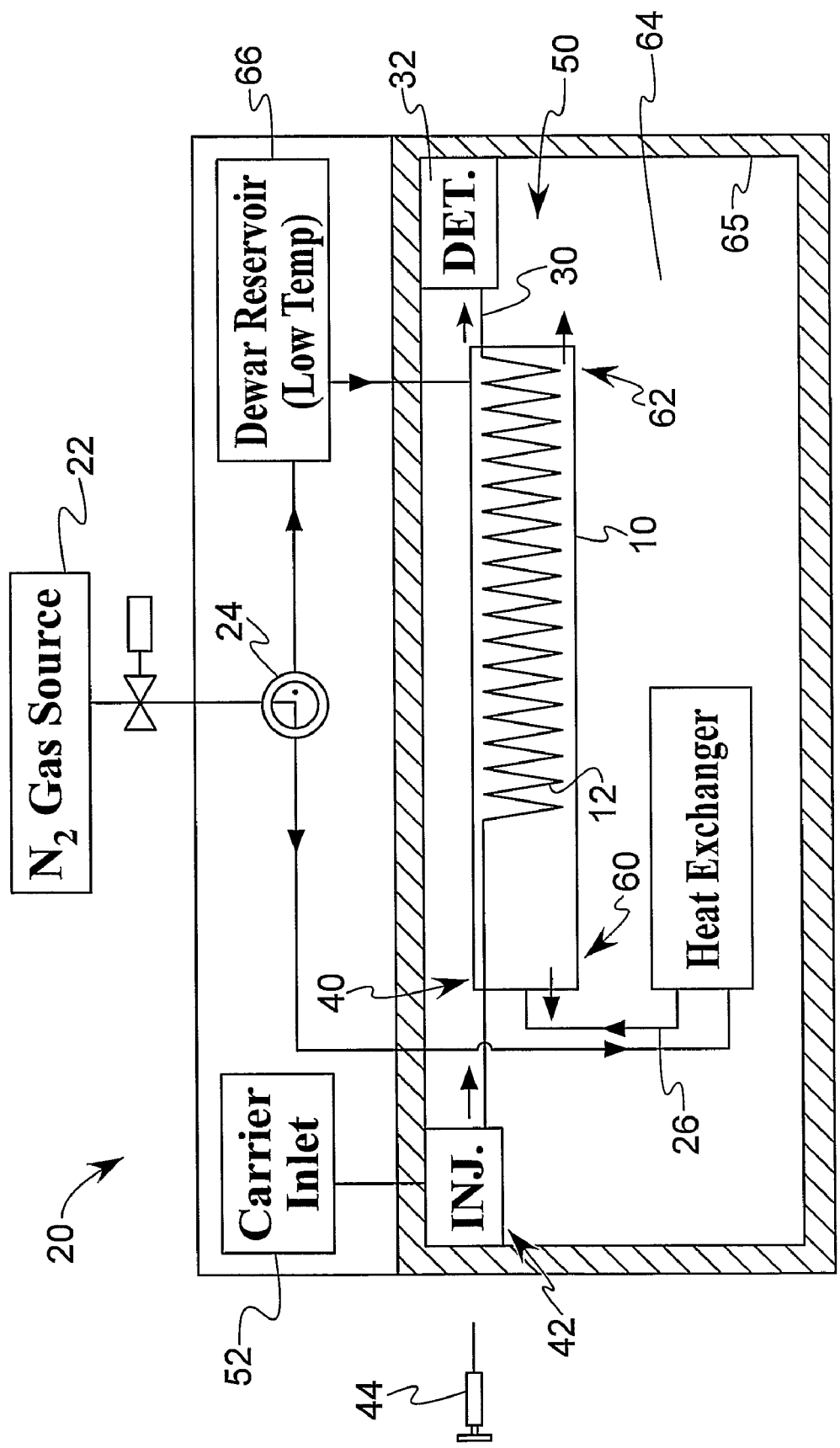
FIG. 2 is a schematic illustration of a gas chromatograph incorporating the compliant column sheath assembly of the present invention.

Referring now to FIG. 2, a gas chromatograph apparatus 20 is illustrated which incorporates the compliant column sheath assembly 10 of the present invention. The gas chromatograph 20 includes insulating walls 65 and an oven or chamber 64 which incorporates the CCSA. As mounted in the gas chromatograph apparatus, the CCSA includes a front end 60 and a back end 62. The gas chromatograph includes an inlet region 40 at the front end of the column where the sample is admitted and received and an outlet region 50 at the back end of the column where the sample exits the column. The inlet region is about 4 cm in length. The inlet region further includes an sample inlet 42 where a sample is first introduced into the column, preferably by a syringe 44.

The gas chromatograph further includes a high pressure heat exchange gas 22 which comprises a gas such as nitrogen or compressed air. The gas is heated by the uniform high temperature of the surrounding air within the oven or chamber (typically controlled by a thermostat) and may be supplied in a bi-directional manner as shown by use of a toggle or solenoid valve 24 which directs the gas flow. This highly directional forced convection of gas can be controlled and adjusted to meet the rapidly changing simultaneous conditions involving distance, temperature, and time that occur within the CCSA. The gas can exhibit both laminar and turbulent flow, which aids in providing axial heating of the column. During the rapid heating provided by the forced convection gas within the CCSA, the interior flow can be unidirectional (i.e., line-of-sight behavior), annular, or have a rotating swirl axial nature. Regardless of whether the gas flow initiates through the front or back end of the CCSA, it continues throughout the axial length of the CCSA. The heat exchange gas flow is of high translational velocity and exhibits its predictable transport and time-programmed heating behavior. The heat exchange gas is preferably introduced into the front or back ends of the CCSA by the use of heat exchanger metal tubing 26 which is connected to the CCSA entrance. The gas chromatograph incorporating the CCSA of the present invention preferably has an operating temperature ranging from −60° C. up to about 400° C.

Alternatively, the heat exchange gas may be heated by the application of vacuum to draw hot gases into the CCSA from the oven.

A carrier gas source 52 is also provided to the inlet region which is controlled by a rapid actuation switching valve (not shown). A number of inert carrier gases may be used to introduce the sample to the inlet region including hydrogen and helium. The preferred carrier gas for use within the OTC is hydrogen or helium having an average velocity of 2 m/sec.

When the gas chromatograph is in use, room temperature gas or in-line cooled gas from a dewar reservoir 66 is introduced from heat exchange gas source 22 to the back end 62 of the CCSA to lower the temperature along the length of the column. A sample is then injected into the front end of the column through sample inlet 42. Organic samples may be in the form of gases, liquids, solids, or multi-phase mixtures. Due to the cooling gas in the CCSA, the sample is positionally stagnated, i.e., the sample does not move inside the column until heated gas is introduced. The cooling gas is then abruptly stopped and heated gas is introduced from source 22 at a temperature of about 300° C. which flows to the front end 60 of the CCSA. The CCSA and the open tubular column within is thus rapidly increased in temperature, while maintaining an intense axial negative gradient throughout the heating process.

The separated materials then exit through outlet 30 where they are analyzed in a detection device 32. A variety of detectors may be used with the CCSA for analysis including a hydrogen flame ionization detector (FID), a time of flight mass spectrometer (TOFMS), an atomic emission detector (AED), or a selective electron capture detector (ECD). Preferred detectors for use in the present invention are a time of flight mass spectrometer (TOFMS) or a flame ionization detector, due to their fast detection speeds.

The CCSA may be used as a component in gas chromatographs which utilize techniques including conventional or faster forms of gas chromatography, multidimensional gas chromatography (MDGC), GCxGC (gas chromatography utilizing a short OTC in combination with a gas chromatograph using a long OTC of different stationary phase), and MDGC-MS (multi-dimensional gas chromatograph coupled with a mass spectrometer). It should be appreciated that the CCSA may be used as a single OTC in a gas chromatograph or in configuration with several OTCs (such as in multi-dimensional GC).

In order that the invention may be more readily understood, reference is made to the following examples which are intended to illustrate the invention, but not limit the scope thereof.

EXAMPLE 1

Figure 3:
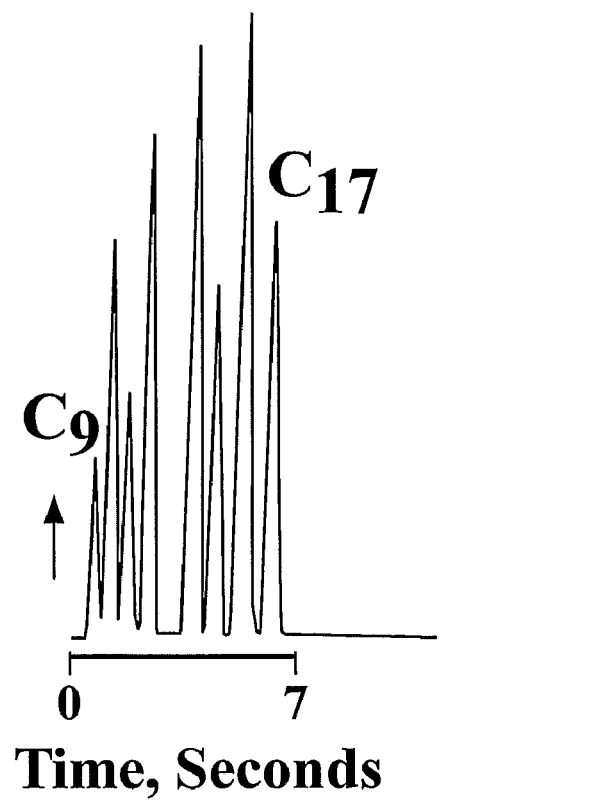
FIG. 3 is a chromatogram illustrating the separation of N-alkane compounds (C9 to C17) achieved using the compliant column sheath assembly of the present invention.

A separation analysis was conducted to simulate the analysis of aviation fuels containing n-alkane compounds. The separation utilized a prototype of a CCSA in accordance with the present invention in conjunction with thermal gradient programmed gas chromatography (TGPGC). As shown in FIG. 3, the separation of C9 to C17 compounds was achieved in 7 seconds.

EXAMPLE 2

Figure 4:
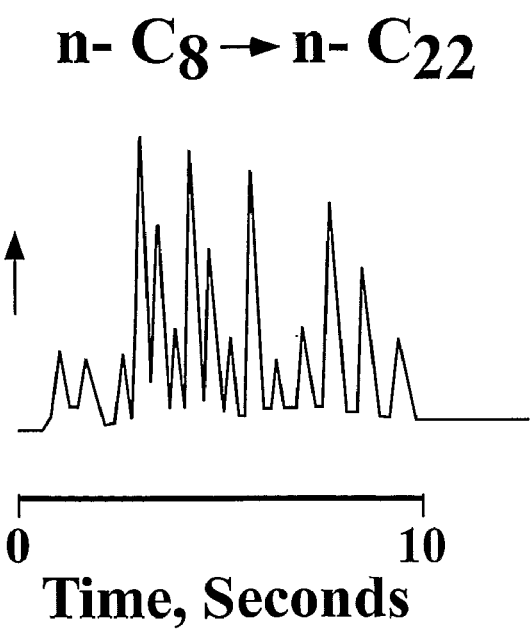
FIG. 4 is a chromatogram illustrating the separation of n-alkane compounds (C8 to C22) achieved using the compliant column sheath assembly of the present invention.

A separation analysis was conducted to simulate distillation of petroleum products. The separation utilized a prototype of a CCSA in accordance with the present invention in conjunction with TGPGC. As shown in FIG. 4, the separation of C8 to C22 compounds was achieved in 10 seconds.

Having described the invention in detail and by reference to preferred embodiments thereof, it will be apparent that modifications and variations are possible without departing from the scope of the invention.

The invention claimed is:

1. A compliant column sheath assembly for use in a gas chromatograph comprising:
    an open tubular column in the form of a helical coil having front and back ends; said column having a length of from about 5 to 15 cm in coiled form and a length of about 1 to 5 meters in straight form;
    a cylindrical sleeve which fits inside the coiled open tubular column; and
    a frame in the form of a metal wire grid which supports said open tubular column, wherein said assembly, when incorporated in a gas chromatograph, provides analysis of a sample in about 2 to 10 seconds.

2. The compliant column sheath assembly of claim 1 further including an insulating sheath.

3. The compliant column sheath assembly of claim 2 wherein said insulating sheath surrounds said frame and said open tubular column.

4. The compliant column sheath assembly of claim 2 wherein said frame supports said open tubular column and said sheath.

5. The compliant column sheath assembly of claim 2 wherein said insulation sheath is comprised of a material selected from woven, braided, thin films, or non-woven insulating materials.

6. The compliant column sheath assembly of claim 1 wherein said open tubular column has a length of about 10 cm in coiled form.

7. The compliant column sheath assembly of claim 1 wherein said open tubular column comprises fused silica tubing.

8. The compliant column sheath assembly of claim 1 further including a heat exchange gas for regulating the heating and cooling of said open tubular column.

9. The compliant column sheath assembly of claim 8 wherein said heat exchange gas comprises nitrogen.

10. The compliant column sheath assembly of claim 8 wherein said heat exchange gas provides a negative axial thermal gradient along the length of said open tubular column.

* * * * *